United States Patent
Gold et al.

(10) Patent No.: US 10,682,322 B2
(45) Date of Patent: Jun. 16, 2020

(54) SUPPORTING IMMUNOMODULATORY AGENT

(71) Applicant: Flexopharm Brain GMBH & Co. KG, Herne (DE)

(72) Inventors: Ralf Gold, Bochum (DE); Aiden Haghikia, Bochum (DE); Ralf Linker, Uttenreuth (DE)

(73) Assignee: FLEXOPHARM BRAIN GMBH & GO. KG, Herne (DE)

(*) Notice: Subject to any disclaimer, the term of this patent is extended or adjusted under 35 U.S.C. 154(b) by 0 days.

(21) Appl. No.: 15/518,481

(22) PCT Filed: Oct. 19, 2015

(86) PCT No.: PCT/EP2015/074179
§ 371 (c)(1),
(2) Date: Apr. 11, 2017

(87) PCT Pub. No.: WO2016/059254
PCT Pub. Date: Apr. 21, 2016

(65) Prior Publication Data
US 2017/0231933 A1    Aug. 17, 2017

(30) Foreign Application Priority Data

Oct. 17, 2014 (DE) .......................... 10 2014 015 314
Oct. 19, 2015 (WO) ................. PCT/EP2015/074179

(51) Int. Cl.
*A61K 31/19* (2006.01)
*A23L 33/12* (2016.01)
(Continued)

(52) U.S. Cl.
CPC .............. *A61K 31/19* (2013.01); *A23L 33/10* (2016.08); *A23L 33/115* (2016.08); *A23L 33/12* (2016.08);
(Continued)

(58) Field of Classification Search
CPC .............................. A61K 31/19; A61K 31/215
See application file for complete search history.

(56) References Cited

U.S. PATENT DOCUMENTS 10,226,443 B2*  3/2019  Scher ..................... A61K 31/20
2007/0248662 A1* 10/2007  Joshi ....................... A61K 9/28
424/452
(Continued)

FOREIGN PATENT DOCUMENTS

WO    2010/105112 A1   9/2010

OTHER PUBLICATIONS

Hofman et al., Digestive Diseases and Sciences, 1997;42(6):1274-1282 (Year: 1997).*
(Continued)

Primary Examiner — San Ming R Hui
(74) Attorney, Agent, or Firm — Wuersch & Gering LLP

(57) ABSTRACT

The invention relates to an agent having immunomodulatory properties for the prevention and/or treatment of autoimmune diseases, said agent comprising one or more $C_3$-$C_8$ carboxylic acids and their physiologically acceptable salts and/or $C_1$-$C_8$ alkyl esters, and their use as immunomodulatory agents for use in prevention and/or treatment of autoimmune related diseases and immune-mediated chronic inflammatory diseases, and dietary supplements with immunomodulating effect comprising one or more $C_3$-$C_8$ carboxylic acids and their physiologically acceptable salts and/or esters comprising $C_1$-$C_8$ alkyl alcohols.

40 Claims, 6 Drawing Sheets

(51) Int. Cl.

| | | |
|---|---|---|
| *A23L 33/16* | (2016.01) | |
| *A61K 31/215* | (2006.01) | |
| *A61K 9/48* | (2006.01) | |
| *A61K 9/20* | (2006.01) | |
| *A23L 33/10* | (2016.01) | |
| *A23L 33/115* | (2016.01) | |
| *A61K 9/00* | (2006.01) | |

(52) U.S. Cl.
CPC ............ *A23L 33/16* (2016.08); *A61K 9/0056* (2013.01); *A61K 9/20* (2013.01); *A61K 9/2004* (2013.01); *A61K 9/48* (2013.01); *A61K 9/4816* (2013.01); *A61K 31/215* (2013.01); *A23V 2002/00* (2013.01)

(56) References Cited

U.S. PATENT DOCUMENTS

2011/0033946 A1* 2/2011 Berenson ............... G01N 30/88
436/129
2011/0112010 A1* 5/2011 Hallett ................. A61K 31/201
514/1.1

OTHER PUBLICATIONS

Puddu et al., Mediators of Inflammation, Aug. 2014,1-9 (Year: 2014).*
Berg J, et al. "Beneficial Effects of Short Chain Fatty Acids on the Course of Experimental Autoimmune Encaphalomyelitis" Journal of Neuroimmunology Oct. 15, 2014, vol. 275, No. 1, p. 59.
Gross CC, et al. "Dimethyl Fumarate Treatment Alters Circulating T Helper Cell Subsets in Multiple Sclerosis" Neurology—Neruoimmunology NeuroInflammation, Dec. 10, 2015, vol. 3, No. 1, pp. e183, XP055312762.
Haghikia A, et al. "Session 042—MS and CNS Inflammatory Disease: Risk Factors in Multiple Sclerosis: Therapeutic Potential of Propionic Acid" AAN Meeting 2016, Apr. 16, 2016, pp. 1-1, XP055312758.
International Search report forms 210 and 237 (German and machine translation English).
Duscha A, et al. "Beneficial Effects of Short Chain Fatty Acids on the Course of Experimental Autoimmune Encephalomyelitis" Journal of Neuroimmunology, Oct. 15, 2014, vol. 275, No. 1, p. 59 Abstract.
Smith PM, et al. "The Microbial Metabolites, Short Chain Fatty Acids, Regulate Colonic Treg Cell Homeostasis" Science ,Aug. 2, 2013, vol. 341, No. 6145, pp. 569-573.
Haghikia A, et al. "Impact of Fatty Acids on CNS Autoimmunity and Their Therapeutic Potential for Multiple Sclerosis" ECTRIMS Online Library, Oct. 7, 2015. Retrieved from the Internet; URL: http://citenpl.internal.epo.org/wf/web/citenpl/citenpl.html [Retrieved on May 17, 2017] abstract.
Furusawa Y, et al. "Commensal Microbe-Derived Butyrate Induces the Differentiation of Colonic Regulatory T Cells" Nature, Dec. 19, 2013, vol. 504, No. 7480, pp. 446-450.
Miller et al., "Clinical Pharmacology of Sodium Butyrate in Patients with Acute Leukemia," European Journal of Cancer and Clinical Oncology 1987, vol. 23, No. 9, pp. 1283-1287 (Abstract).
This application is related to co-pending U.S. Appl. No. 15/769,282 entitled "Supporting Immunomodulatory Agent," filed Apr. 18, 2018.

* cited by examiner

SUPPORTING IMMUNOMODULATORY AGENT

CROSS REFERENCE TO RELATED APPLICATIONS

This application is a National Stage application under 35 U.S.C. § 371 of PCT/EP2015/074179, filed on Oct. 19, 2015, which claims priority to DE 10 2014 015 314.2, filed on Oct. 17, 2014.

TECHNICAL FIELD

The invention relates to agents with immunomodulatory activity for the treatment of autoimmune and immune-mediated chronic inflammatory diseases, wherein said agents comprise one or more $C_3$-$C_8$ carboxylic acids and their physiologically acceptable salts and/or esters with $C_1$-$C_8$ alkyl alcohols.

BACKGROUND

In autoimmune-related diseases, the body's own tissues are targeted as a result of a dysfunctional immune response, for example, in multiple sclerosis (MS) and in immune-mediated chronic inflammatory diseases that cause inflammation in various tissues including the intestines (Crohn's disease, ulcerative colitis), in the skin (psoriasis) or of the joints (spectrum of rheumatic diseases). Common to all these disease conditions, is that due to the inflammation other disease conditions may occur with an above-average frequency, such as excess weight, high blood pressure, arteriosclerosis, cardiac infarction, and stroke.

Recent knowledge gained in the field of microbiomes has shown that nutrition, the intestinal microbiome, and the local cellular immune response are interconnected. This suggests that dietary measures can have an influence on the cellular immune response and thus-on the course of autoimmune diseases and immune-mediated chronic inflammatory diseases.

An essential role in autoimmune diseases and in immune-mediated chronic diseases is the action of regulatory T cells (Treg) and the diversity of the microbiome. Despite many unanswered questions concerning which components of the microbiome are actually responsible for a differentiated adaptive immune response in the intestinal region, a great amount of empirical information has been collected suggesting individual types of bacteria and their bacterial metabolites exert a considerable influence on the systemic immune response in connection with autoimmune diseases and immune-mediated chronic inflammatory diseases, for example, in case of—type 1 diabetes and Crohn's disease.

It has been found that the intestinal microbiome can be influenced by the type of nutrition consumed and is able to adapt to conditions created by a given kind of food. This means that an intestinal microbiota unfavorable to the immune status of a patient can be changed by taking suitable dietary measures aimed at improving the immune status of the patient.

The intestinal microbiome and dietary habits, such as a high salt intake, have recently been identified as environmental factors in the pathogenesis of multiple sclerosis (MS), a prototype autoimmune-related disease of the central nervous system mediated by T cells. The influence of the intestinal microbiome on chronic inflammatory diseases of the intestines and type 1 diabetes was mentioned above. Distinctive characteristics of the intestinal microbiota have also been detected in patients suffering from type 2 diabetes.

SUMMARY OF THE INVENTION

Fatty acids have a major influence on regulatory T cells and the intestinal microbiome. It has been reported that long-chain fatty acids exert an inhibiting-effect on both regulatory T cells and intestinal microbiota. It has now surprisingly been found that short-chain fatty acids have a positive effect on the proliferation and amount of regulatory T cells in the intestines and blood. This was particularly the case for propionic and butyric acid, and their physiologically acceptable salts and/or esters. Moreover, it has been determined that the targeted administration of short-chain fatty acids with three to eight carbon atoms has a positive influence on the development and course of neuroimmunological diseases with neurodegenerative aspects like MS.

Accordingly, the invention relates to an agent with immunomodulatory activity of comprising one or more C3-C8 carboxylic acids and their physiologically acceptable salts and/or esters with C1-C8 alkyl alcohols.

DETAILED DESCRIPTION OF THE INVENTION

Figure 1:
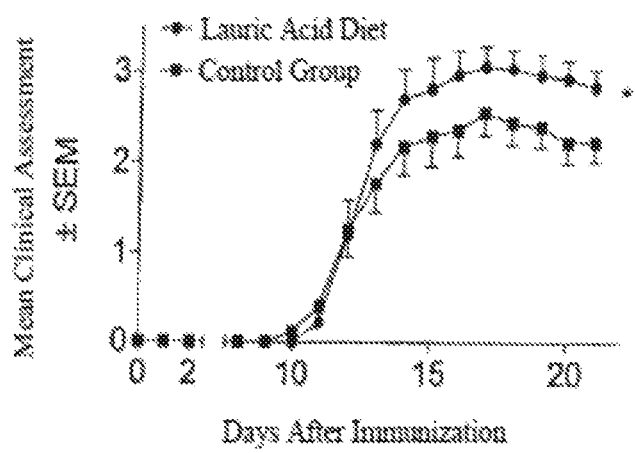
FIG. 1 is a graph showing the results of a study comparing the effect of a lauric acid diet compared to a control group on SEM clinical assessments in a mouse experimental autoimmune encephalomyelitis (EAE) model.

The agents claimed in the present invention have immunomodulatory activity when used as a dietary supplement or when used in combination with a medical agent for treating autoimmune related diseases and immune-mediated chronic inflammatory diseases as well as their secondary pathologies.

Autoimmune-related diseases referred to here are primarily those-whose development is associated with abnormalities in the intestinal microbiota and in the occurrence of regulatory T cells. For example, these include neurodegenerative diseases such as MS or other autoimmune-related diseases such as psoriasis, IBD, rheumatoid arthritis and the various types of diabetes.

The inventive effect is limited to short-chain carboxylic acids, i.e. those with no more than eight carbon atoms, longer chained carboxylic acids opposite effects are observed. Carboxylic acids with twelve or more carbon atoms usually exert a negative effect on the development and course of the disease.

Especially preferred C3-C8 carboxylic acids are propionic acid and butyric acid as well as their salts and esters.

The term carboxylic acids is understood to mean monocarboxylic acids preferably of the straight-chain configuration. The monocarboxylic acids may also contain double bonds. However, preferred are straight-chained saturated carboxylic acids, in particular those with three or four carbon atoms.

The alkali and alkaline earth metal salts are most preferable as physiologically acceptable salts. Additionally, salts of physiologically safe or essential heavy metals, for example zinc or iron can be used. Of the alkali metals, sodium and potassium are especially preferred, as are magnesium and calcium of the alkaline earth metals.

Regarding esters, preference is given to methyl and ethyl esters.

The carboxylic acids of the present invention and their esters and salts may be combined with fumaric acid esters and salts, for example with dimethyl fumarate and salts of fumaric acid monomethyl ester, as well as with—vitamins A and D.

The inventive agent may be provided in any marketable form. Preferred forms are capsules and tablets. Capsules are used in the case of liquid carboxylic acids or esters. Acids in the form of salts, for example sodium propionate or sodium butyrate, may be compressed into tablets by customary tableting means.

As a rule, the capsules and tablets contain a unit dose of 0.2 to 5 g, in particular of 0.5 to 3 g.

According to the invention, the agents can be administered for a daily intake of up to 10 g. However as a rule, one capsule or tablet with a maximum dose of 5 g per day will be sufficient for treatment.

Moreover, the invention also relates to the use of C3-C8 carboxylic acids, their physiologically acceptable salts and esters with C1-C8 alkyl alcohols as immunomodulators useful for treating autoimmune-related diseases. These carboxylic acids may also be used to produce drugs in intended to accompany the therapy of for autoimmune diseases, and also as a dietary supplement having immunomodulating activity.

The inventive acids, in particular propionic acid and butyric acid have an influence on the bowel physiology and the microbiome present there. In this way, they have an impact on the composition of the microbiome. The number of bacteria degrading propionate and butyrate increases significantly while at the same time the normal intestinal microbiota are only slightly affected. In contrast, long-chain carboxylic acids (lauric acid) cause the number of Provotellaceae and some families of Phylum Bacteroidetes present in mice to reduce significantly.

Mice treated with propionic acid showed changes of the microbiota accompanied by increase in the number of regulatory T cells (CD4+ CD25+ Foxp3+ Treg). Gene expression profiling of signature cytokines showed increased values with respect to TGFβ1, IL-10—generally anti-inflammable messengers—and Foxp3 in mice with experimental autoimmune encephalomyelitis (EAE) fed propionic acid.

Moreover, the aliphatic chain length of the carboxylic acids also affects the Th1/Th7-mediated autoimmunity as well as the regulatory response of Treg in an in vivo mouse model. Mice fed a lauric acid enriched diet showed in the EAE model a significant reduction of TH1 and TH17 cells in the small intestine and at the same time an accumulation of Th1/Th17 in the central nervous system which suggests that the control of the inflammatory cells has been transferred from the intestine to the brain/spinal cord. Under otherwise similar conditions, propionic acid caused a significant increase of TGFβ1, IL-10, and Foxp3. These results taken together and in comparison to a control group, showed a change to the worse following the onset of induced disease in the MS mouse model of MS with a diet comprising long-chain fatty acids, whereas in mice that were prophylactically given propionic acid a significant improvement was observed.

As a result, propionic acid appears to be able to change- and normalize a compromised balance occurring between Treg and effector T cells (Th1/Th17). MS patients show such a disturbed balance.

Moreover, the data obtained attest to the fact that the inventive carboxylic acids favorably influence the human fat hormone metabolism. In this context, by administering these acids the adiponectin concentration in the blood statistically significantly increased. In comparison, resistin behaves conversely. In the case of the short-chain carboxylic acids the serum leptin content also increases. Leptin serves to inhibit the appetite and hunger signals and in this way plays an important role for the regulation of the fat metabolism in mammals including human beings.

Adiponectin is produced by fat cells. If these are empty, adiponectin production increases. Obese people have a low adiponectin level, insulin to become less effective. A low level of adiponectin in conjunction with genetic factors results in a higher risk of developing diabetes mellitus and at the same time causes vascular damage long before diabetes is diagnosed. People having a high adiponectin level are protected against the development of diabetes.

EXAMPLES

Experimental Findings

Mice kept under standardized conditions were fed on a normal diet enriched with long-chain fatty acids (30.9% lauric acid) and additionally with 200 µl of propionate daily administered orally. The propionate was given either at the time of disease induction (DI) or at the onset of the disease (OD).

For the induction of EAE the mice were anesthetized and administered two subcutaneous injections of a 50 µl emulsion applied to the left and right tail basis and comprising a total of 200 µg $MOG_{35-55}$ (myelin oligodendrocyte glycoprotein) and 200 µg Freund's adjuvant (CFA) with 4 mg/ml of *M. tuberculosis*. Pertussistoxin (200 mg/mouse) was given intraperitoneally on day 0 and 2 after the induction. The clinical assessment took place on a daily basis using a 5-point scale (SEM). The assessment was as follows:

0=normal
1=Tail paralysis impairing raising
2=Gait ataxia
3=Paraparesis of hind legs
4=Tetraparesis
5=Death Mice showing SEM 4 or 5 were excluded.
Results are shown in the Figures.

Example 1

FIG. 1 shows results of a mouse population fed a diet enriched with lauric acid in comparison to a control group. Onset of disease occurred approximately ten days after induction with the disease reaching its peak at seventeen days. With respect to SEM scores, the control group scored better than the group fed the diet enriched with lauric acid.

Example 2

Figure 2:
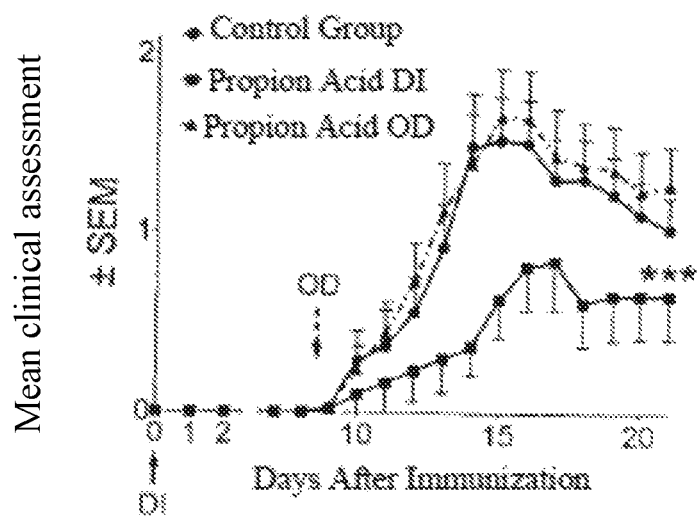
FIG. 2 is a graph showing the effect of a propionic acid diet initiated at the time of disease induction (DI) or at the time of onset of symptoms (OD) compared to a control group on SEM in the mouse EAE model.

FIG. 2 shows a results of a comparison of a mouse population fed a propionic acid diet versus a control group. The propionic acid was administered either on the day of induction (DI) or on the day of onset of disease (OD). It was found that the group given propionic acid on the day the onset of disease occurred (OD) showed a significantly less favorable disease course than the control group.

Figure 3:
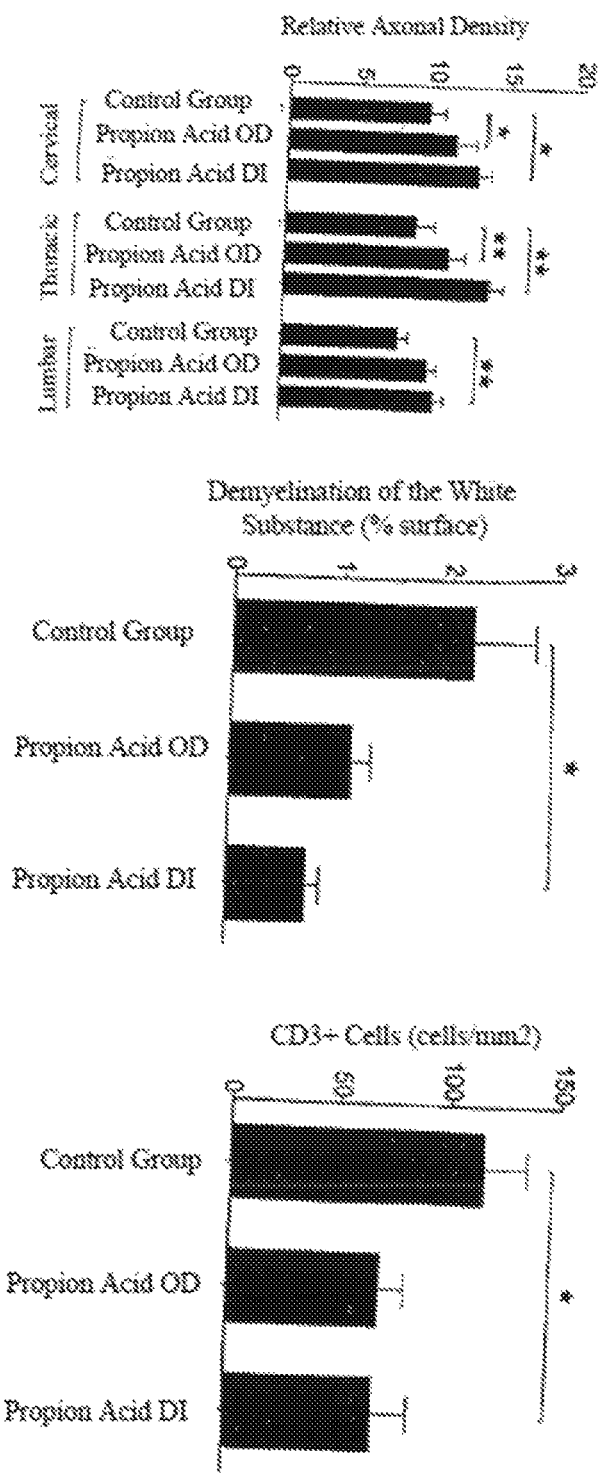
FIG. 3: is a graph showing the effect of propionic acid diet initiated at the time of disease induction (DI) or at the time of onset of symptoms (OD) compared to a diet control group on relative axonal density, demyelination in the white matter, and CD3+ cells in the mouse EAE model.

The influence of propionic acid on the relative axonal density, the demyelination of the white matter, and the number of CD3+-cells is shown in FIG. 3. In general, administration of propionic acid showed a significant improvement compared to the control group.

Figure 4:
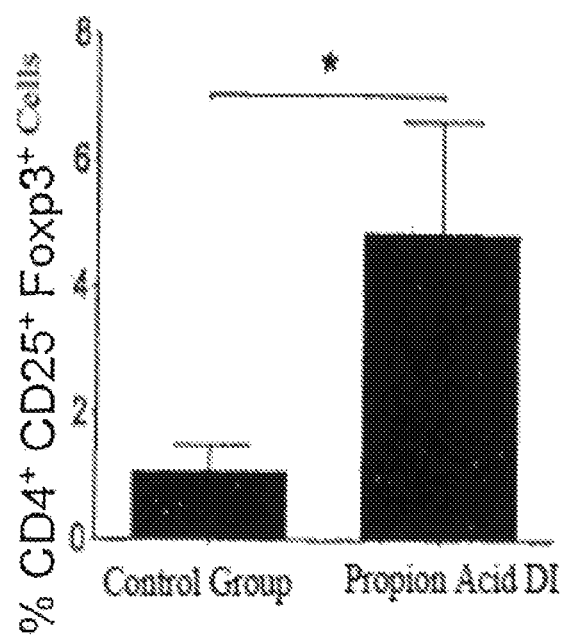
FIG. 4: is a graph showing the effect of propionic acid diet initiated at the time of disease induction (DI) compared to a control group on levels of CD4+ CD25+ Foxp3 cells in mouse EAE model.

FIG. 4 shows the effect of administration of propionic acid on the CD4+-CD25+ Foxp3 cells expressed as a significant increase in comparison to the control group.

Example 3

Figure 5:
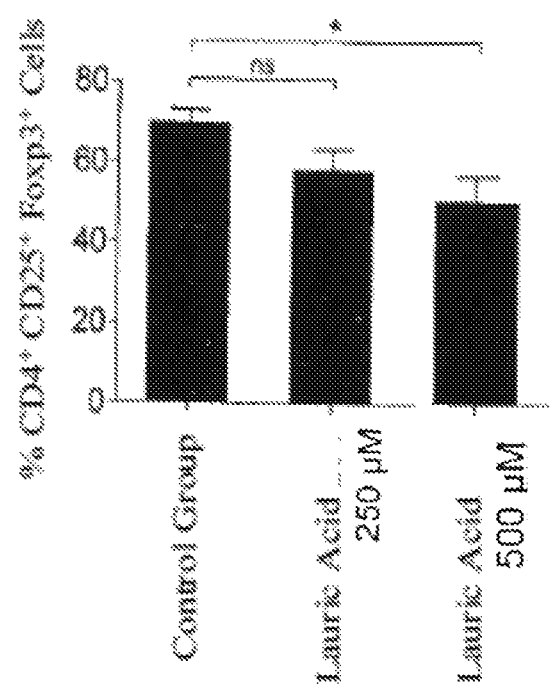
FIG. 5 is a graph showing the effect of lauric acid diet (250 µM and 500 µM) initiated at the time of disease induction (DI) compared to a control group on levels of CD4+ CD25+ Foxp3 cells in mouse EAE model.

FIG. 5 shows the effect of a lauric acid enriched diet on CD4+ CD25+ Foxp3 cells in comparison to a control group. The administration of the long-chain fatty acids resulted in a reduction of the T cells versus the control value. The percentage reduction was dependent on concentration of the long-chain fatty acids.

Example 4

Figure 6:
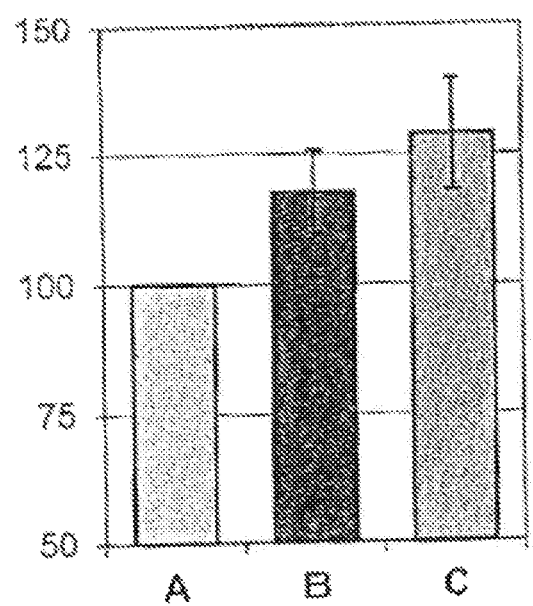
FIG. 6 is a graph showing the effect of administration of sodium propionate in a clinical study in ten patients on adiponectin levels. Column A shows the level of adiponectin in patients prior to administration of sodium propionate; column B shows the level of adiponectin in patients administered 500 mg of sodium propionate each in the morning and evening; and column C shows the level of adiponectin in patients four weeks after the administration of sodium propionate had been terminated.

FIG. 6 shows the effect of administration of sodium propionate on the adiponectin levels based on evaluation of a study involving 10 patients. Column A shows the condition prior to the administration of sodium propionate. Column B shows the condition after administration of a daily dose of 1,000 mg sodium propionate, with half of it administered in the morning and the other half administered in the evening. Column C shows the adiponectin level 4 weeks after the administration of sodium propionate had been terminated. The adiponectin levels increase statistically significantly to 120 to 130% and the effect lasts longer than the administration duration.

The invention claimed is:

1. A method of treating multiple sclerosis and/or psoriasis in a subject in need of such treatment, comprising administering orally to said subject a composition comprising one or more $C_3$-$C_8$ carboxylic acids, their physiologically acceptable salts and/or esters, in a dosage amount effective for treating multiple sclerosis and/or psoriasis, wherein the one or more $C_3$-$C_8$ carboxylic acids are propionic acid and/or butyric acid.

2. The method of claim 1, wherein the physiologically acceptable salts are salts of sodium, potassium, magnesium, calcium, zinc and/or iron.

3. The method of claim 2, wherein the carboxylic acid salt is sodium propionate.

4. The method of claim 2, wherein the carboxylic acid salt is sodium butyrate.

5. The method of claim 1, wherein the physiologically acceptable esters are $C_1$-$C_8$ alkyl esters.

6. The method of claim 5, wherein the physiologically acceptable esters are methyl and/or ethyl esters.

7. The composition of claim 1, wherein the subject is a human.

8. The method of claim 1, wherein the composition of one or more $C_3$-$C_8$ carboxylic acids, their physiologically acceptable salts and/or esters is administered orally in a unit dose in a dietary supplement.

9. The method of claim 3, wherein the sodium propionate is administered orally in a unit dose in a dietary supplement.

10. The method of claim 8, wherein the dietary supplement comprises a unit dose of about 0.2 g to about 5 g.

11. The method of claim 9, wherein the dietary supplement comprises a unit dose of about 0.2 g to about 5 g.

12. The method of claim 10, wherein the dietary supplement comprises a unit dose of about 0.5 g to about 3 g.

13. The method of claim 11, wherein the dietary supplement comprises a unit dose of about 0.5 g to about 3 g.

14. The method of claim 1, wherein the one or more $C_3$-$C_8$ carboxylic acids, their physiologically acceptable salts and/or esters is administered orally in a dietary supplement in a total daily dose of about 0.2 g to about 10 g.

15. The method of claim 14, wherein the total daily dose is about 0.2 g to about 5 g.

16. The method of claim 3, wherein the sodium propionate is administered orally in a dietary supplement in a total daily dose of about 0.2 g to about 10 g.

17. The method of claim 16, wherein the total daily dose is about 0.2 g to about 5 g.

18. The method of claim 1, wherein the disease being treated is multiple sclerosis.

19. The method of claim 3, wherein the disease being treated is multiple sclerosis.

20. A method of treating multiple sclerosis and/or psoriasis in a subject in need of such treatment comprising administering orally to said subject an effective dose of a composition comprising
one or more $C_3$-$C_8$ carboxylic acids, their physiologically acceptable salts and/or esters, wherein the one or more $C_3$-$C_8$ carboxylic acids are propionic acid and/or butyric acid;
and at least one additional therapeutic agent,
wherein the method treats multiple sclerosis and/or psoriasis.

21. The method of claim 20, wherein the at least one additional therapeutic agent is a fumaric acid ester derivative, Vitamin A, and/or Vitamin D.

22. The method of claim 21, wherein the fumaric acid ester derivative is dimethyl fumarate or salts of fumaric acid monomethyl ester.

23. The method of claim 20, wherein the disease being treated is multiple sclerosis.

24. The method of claim 20, wherein the one or more $C_3$-$C_8$ carboxylic acids, their physiologically acceptable salts and/or esters is sodium propionate and the at least one additional therapeutic agent is dimethyl fumarate.

25. The method of claim 1, wherein the disease being treated is psoriasis.

26. The method of claim 3, wherein the disease being treated is psoriasis.

27. A method of treating multiple sclerosis in a human subject in need thereof, comprising administering orally to said subject a composition comprising one or more $C_3$-$C_8$ carboxylic acids, their physiologically acceptable salts and/or esters, in a dosage amount effective for treating multiple sclerosis, wherein the one or more $C_3$-$C_8$ carboxylic acids are propionic acid and/or butyric acid.

28. The method of claim 27, wherein the one or more $C_3$-$C_8$ carboxylic acids, their physiologically acceptable salts and/or esters is sodium propionate.

29. The method of claim 28, wherein the sodium propionate is administered orally in a unit dose in a dietary supplement.

30. The method of claim 29, wherein the dietary supplement comprises a unit dose of about 0.2 g to about 5 g.

31. The method of claim 30, wherein the dietary supplement comprises a unit dose of about 0.5 g to about 3 g.

32. The method of claim 28, wherein the sodium propionate is administered orally in a dietary supplement in a total daily dose of about 0.2 g to about 10 g.

33. The method of claim 32, wherein the total daily dose is about 0.2 g to about 5 g.

34. A method of treating psoriasis in a human subject in need thereof, comprising administering orally to said subject a composition comprising one or more $C_3$-$C_8$ carboxylic acids, their physiologically acceptable salts and/or esters, in a dosage amount effective for treating psoriasis, wherein the one or more $C_3$-$C_8$ carboxylic acids are propionic acid and/or butyric acid.

35. The method of claim 34, wherein the one or more $C_3$-$C_8$ carboxylic acids, their physiologically acceptable salts and/or esters is sodium propionate.

36. The method of claim 35, wherein the sodium propionate is administered orally in a unit dose in a dietary supplement.

37. The method of claim 36, wherein the dietary supplement comprises a unit dose of about 0.2 g to about 5 g.

38. The method of claim 37, wherein the dietary supplement comprises a unit dose of about 0.5 g to about 3 g.

39. The method of claim 35, wherein the sodium propionate is administered orally in a dietary supplement in a total daily dose of about 0.2 g to about 10 g.

40. The method of claim 39, wherein the total daily dose is about 0.2 g to about 5 g.

* * * * *